(12) United States Patent
Rossi et al.

(10) Patent No.: US 7,291,128 B2
(45) Date of Patent: Nov. 6, 2007

(54) MEDICAL KIT COMPRISING A CATHETER, A NEEDLE AND ITS CASE

(75) Inventors: Daniel Rossi, Meriel (FR); Jean-Max Huet, Clichy (FR)

(73) Assignee: Vygon, Ecouen (FR)

( * ) Notice: Subject to any disclaimer, the term of this patent is extended or adjusted under 35 U.S.C. 154(b) by 617 days.

(21) Appl. No.: 10/487,265

(22) PCT Filed: Feb. 7, 2003

(86) PCT No.: PCT/FR03/00393

§ 371 (c)(1),
(2), (4) Date: Feb. 19, 2004

(87) PCT Pub. No.: WO03/066151

PCT Pub. Date: Aug. 14, 2003

(65) Prior Publication Data

US 2004/0243060 A1    Dec. 2, 2004

(30) Foreign Application Priority Data

Feb. 8, 2002 (FR) .................................. 02 01600
Feb. 5, 2003 (FR) .................................. 03 01313

(51) Int. Cl.
*A61M 5/00* (2006.01)
*A61M 5/178* (2006.01)
(52) U.S. Cl. .................................. 604/110; 604/164.08

(58) Field of Classification Search ................ 604/110, 604/171, 164.08, 164.01, 164.09, 164.12, 604/263, 533, 535, 115, 116, 162, 164.07, 604/181, 187, 165.02, 192, 193, 195, 197, 604/198
See application file for complete search history.

(56) References Cited

U.S. PATENT DOCUMENTS

| | | | | |
|---|---|---|---|---|
| 5,129,884 A | * | 7/1992 | Dysarz | 604/164.08 |
| 5,456,668 A | * | 10/1995 | Ogle, II | 604/110 |
| 5,520,654 A | * | 5/1996 | Wahlberg | 604/164.08 |
| 5,651,772 A | * | 7/1997 | Arnett | 604/164.01 |
| 5,957,887 A | * | 9/1999 | Osterlind et al. | 604/110 |
| 6,325,781 B1 | * | 12/2001 | Takagi et al. | 604/198 |
| 6,969,376 B2 | * | 11/2005 | Takagi et al. | 604/263 |

* cited by examiner

*Primary Examiner*—Nicholas D. Lucchesi
*Assistant Examiner*—Matthew F. DeSanto
(74) *Attorney, Agent, or Firm*—Levine & Mandelbaum (57) ABSTRACT

A sheath is provided with a stationary deflector disposed on the path of the slider so that contact between the slider and the deflector causes the slider to be inclined and consequently causes the needle to be inclined inside the sheath. A return mechanism is provided so as to push the inclined slider back in the opposite direction so that the point of the inclined need is prevented from moving. This disposition ensures that the needle cannot escape from the sheath after it has been used.

17 Claims, 12 Drawing Sheets

FIG. 1

FIG_1

MEDICAL KIT COMPRISING A CATHETER, A NEEDLE AND ITS CASE

BACKGROUND OF THE INVENTION

The invention relates to a medical assembly comprising a short catheter, a puncturing needle engaged in the catheter to enable the catheter to be inserted into a body, and a tubular sheath detachably coupled to the catheter to receive the entire needle after the needle has been used for puncturing and once it has been withdrawn from the catheter.

Numerous embodiments of such an assembly are known (U.S. Pat. Nos. 5,273,540, 6,077,244, 6,193,690, 5,879,331, WO 95/19193).

Publications U.S. Pat. No. 5,879,331 and WO 95/19193 describe embodiments in which the sheath presents a longitudinal slot between a distal outlet for connection to the catheter and an opposite proximal end, and carries a slider mounted to slide along the slot, the slider presenting an internal portion situated inside the sheath and constituting a base for the needle, and an external portion situated on the sheath and enabling the slider to be moved manually so as to cause it to slide from a distal position in which the needle passes through the catheter to a proximal position in which the needle is totally withdrawn from the catheter and retracted into the sheath.

The problem arises of ensuring that once the needle has been retracted into the sheath in this way and after the sheath and the catheter have been separated, it is not possible under the effect of inappropriate handling of the slider for the needle to be moved back out from the sheath through the coupling outlet, and various solutions have been proposed for this purpose.

In the solution described in U.S. Pat. No. 5,879,331, the sheath is provided with a moving arm which tilts when it is contacted by the slider, and presses against the needle close to its sharp end so as to incline the needle in such a manner that it is no longer on the axis of the catheter coupling outlet.

In an embodiment described in publication WO 95/19193 the sheath is shaped internally, close to the end of the stroke of the slider towards said proximal end of the sheath, so that, at the end of the stroke, contact between the slider and the sheath causes the slider to be inclined and consequently causes the needle to be inclined inside the sheath.

SUMMARY OF THE INVENTION

The present invention seeks to provide anti-pricking safety while simplifying the device and reducing its overall dimensions.

The invention achieves this by providing a stationary deflector (13; 16; 22) disposed inside the sheath on the path of the slider close to the end of the stroke of the slider towards said proximal end (3b) of the sheath, so that contact between the slider and the deflector causes the slider to be inclined and consequently causes the needle to be inclined inside the sheath, and return means designed for subsequently pushing the inclined slider back towards the distal end of the sheath so that the tip of the needle is prevented from moving.

The return means are preferably constituted by means provided on the slider and means provided on the sheath, said means being disposed so as to come into contact at the end of the stroke of the slider towards said proximal end, and cooperating so that the slider is pushed back in the opposite direction by a resilient effect.

Preferably, the tip of the inclined needle is pushed back until it becomes set in the wall of the sheath or in the wall of a coupling mounted at the distal end of the sheath.

Preferably, the tip of the inclined and pushed-back needle is received in a groove made around the needle outlet of the sheath.

DESCRIPTION OF THE DRAWINGS

Non-limiting embodiments of an assembly of the invention are described below by way of example with reference to the figures of the accompanying drawings, in which.

DESCRIPTION OF THE PREFERRED EMBODIMENT

The assembly shown in the figures comprises a short catheter (1), a puncture needle (2) for enabling the catheter to be inserted into a vein, a cylindrical sheath (3) connected detachably to the catheter, and a slider (4) slidably mounted on the sheath so as to withdraw the needle into the tube after puncturing.

The sheath (3) has a distal end (3a) arranged or provided with a coupling (19) for connecting it to the catheter, an opposite proximal end (3b), and a longitudinal lateral slot (3c) situated between its ends. The sheath carries the slider (4) mounted to slide along the slot and presenting an external portion (4a) situated on the sheath and an internal portion (4b) situated inside the sheath, these two portions being connected to each other through the slot in the sheath.

The external portion (4a) is designed to enable the slider to be pushed so as to slide along the slot.

The internal portion (4b) is fixed to the needle and constitutes a hollow base for the needle which is closed by an air-vent filter (5) and which is fitted with a valve which opens under the injection pressure of a syringe.

Figure 7:
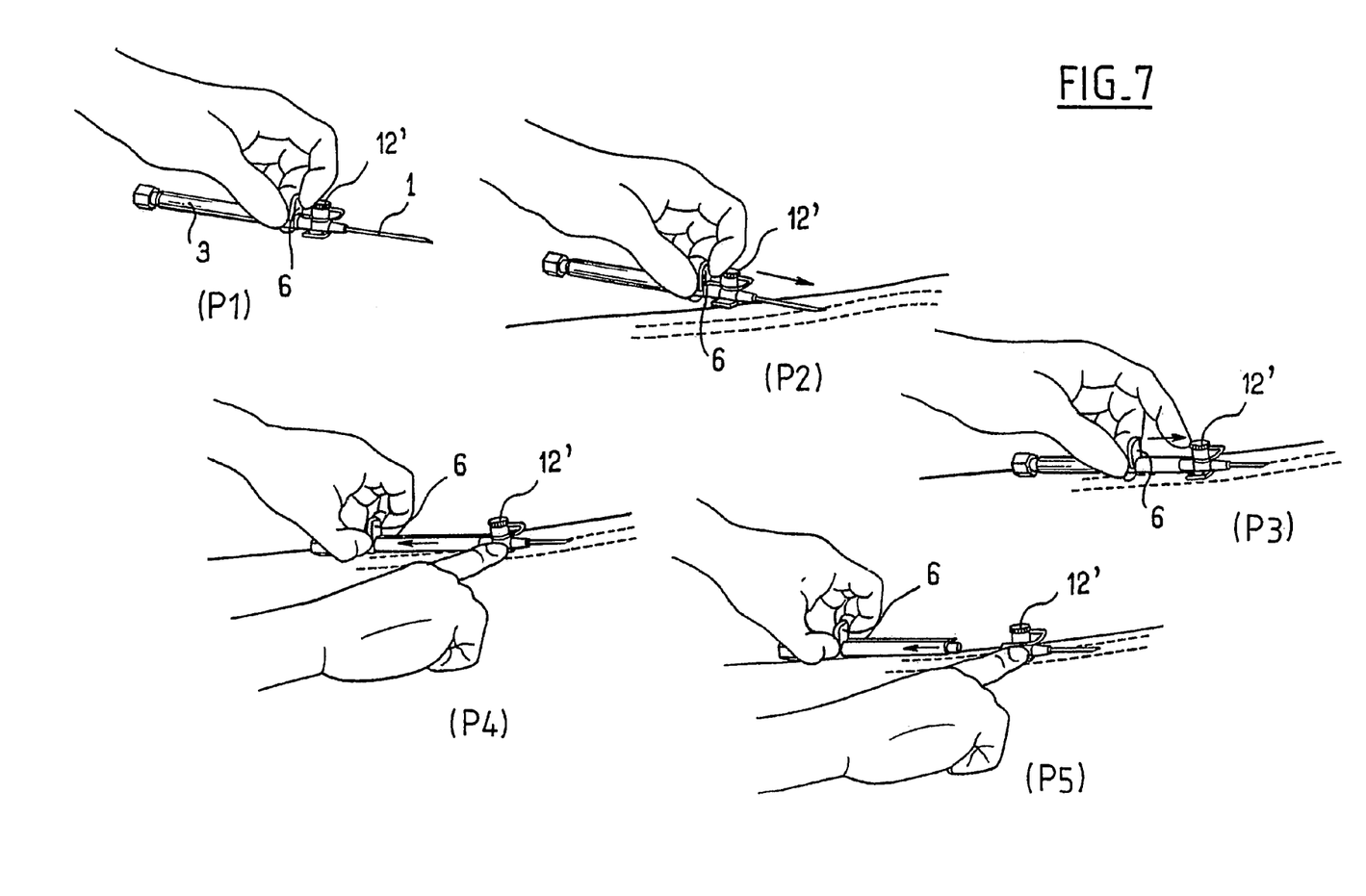
FIG. 7 is a diagram of successive stages while implementing an assembly of the invention.
Figure 8:
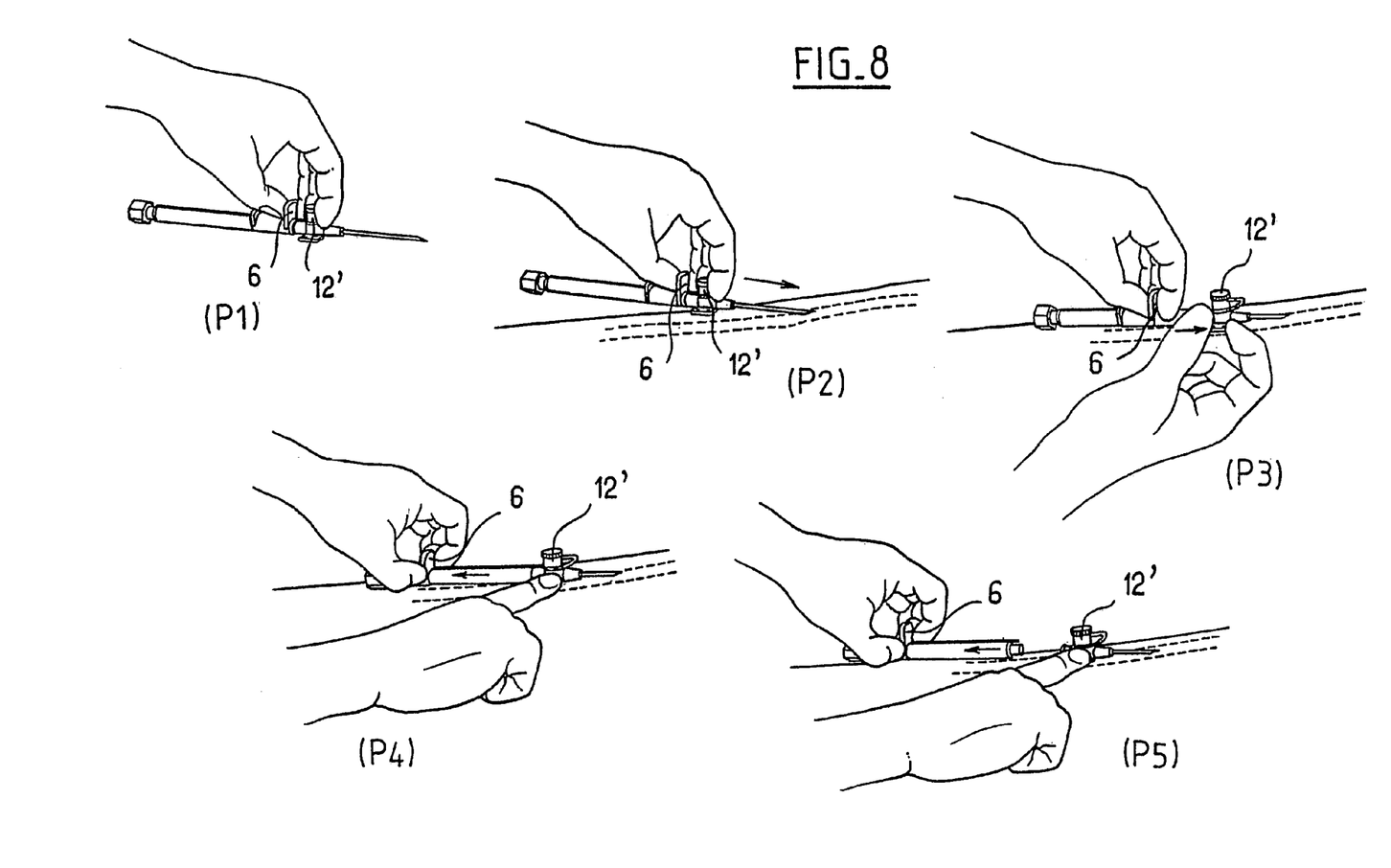
FIG. 8 is a diagram comparable to that of FIG. 7 for a variant implementation process.
Figure 9:
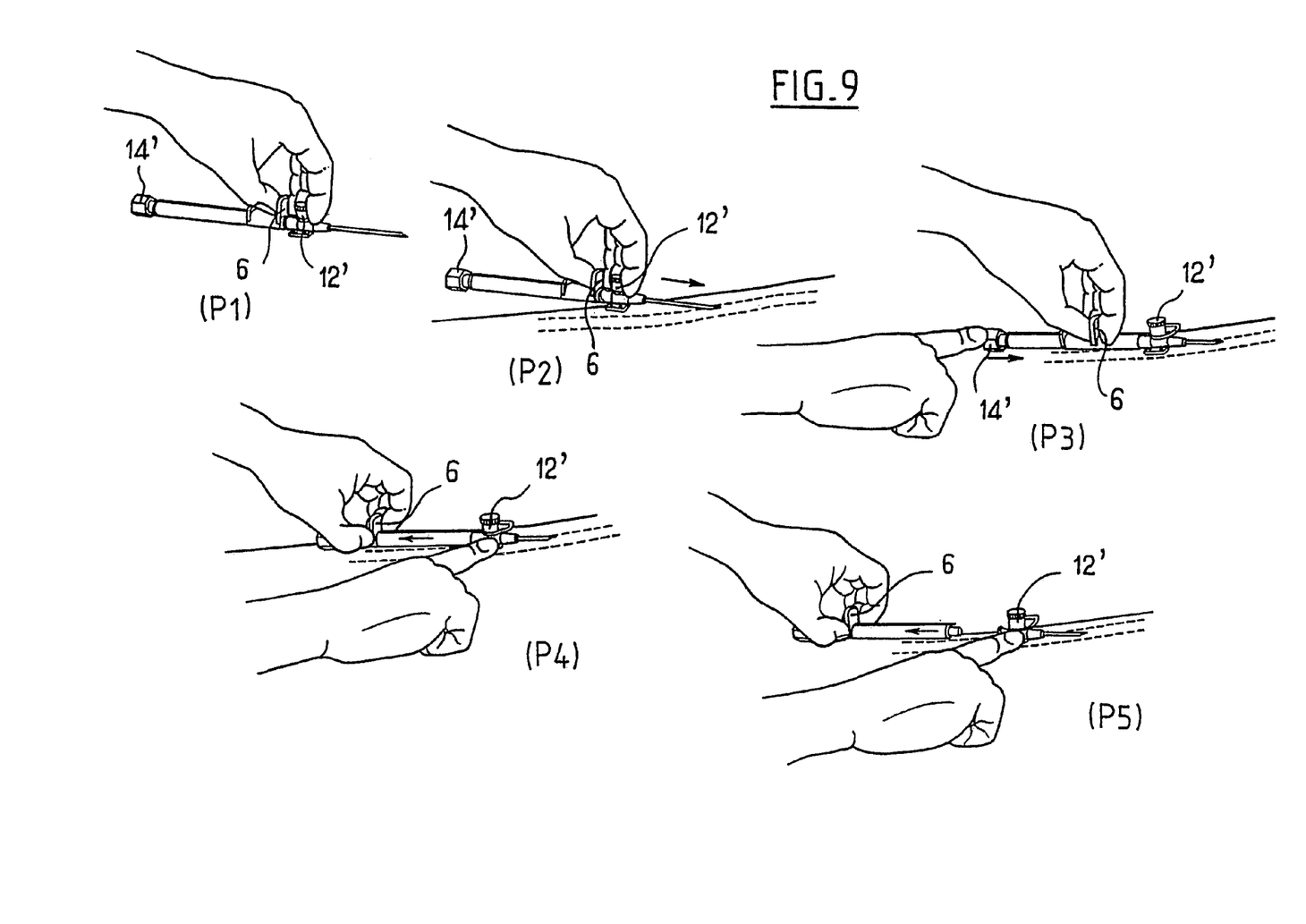
FIG. 9 is a diagram corresponding to FIG. 7 for another variant implementation.

In the examples shown, the external portion (4a) of the slider presents a transverse lug (6) which the user can drive in various ways in order to perform puncturing and subsequently to withdraw the needle, as shown in FIGS. 7 to 9.

The catheter is provided with a socket coupling (7) of known type, and the distal end (3a) of the sheath is designed to penetrate into said coupling or is provided with a suitable coupling (19).

The catheter coupling presents an external bead (8) placed behind the coupling and the distal end (3a) of the sheath or the coupling (19) of the sheath presents a forwardly-directed tongue (9) which takes up a position on the coupling in front of the bead when the base is connected to the catheter, but which is sufficiently flexible to be capable of being forced over the bead when the sheath is separated from the coupling.

The distal end or the distal coupling (19) of the sheath is normally closed by a transverse partition (10') which allows the needle to pass axially therethrough, e.g. via a hole (11).

The catheter coupling (7) may have a lateral inlet (12) in conventional manner for enabling injections to be performed. This inlet (12) is closed by a cap (12').

The tubular sheath has stationary deflectors for moving the needle away from its axis after it has been withdrawn into the sheath, so as to ensure that the needle cannot move back out through the distal end of the sheath under inappropriate handling of the slider.

Figure 1:
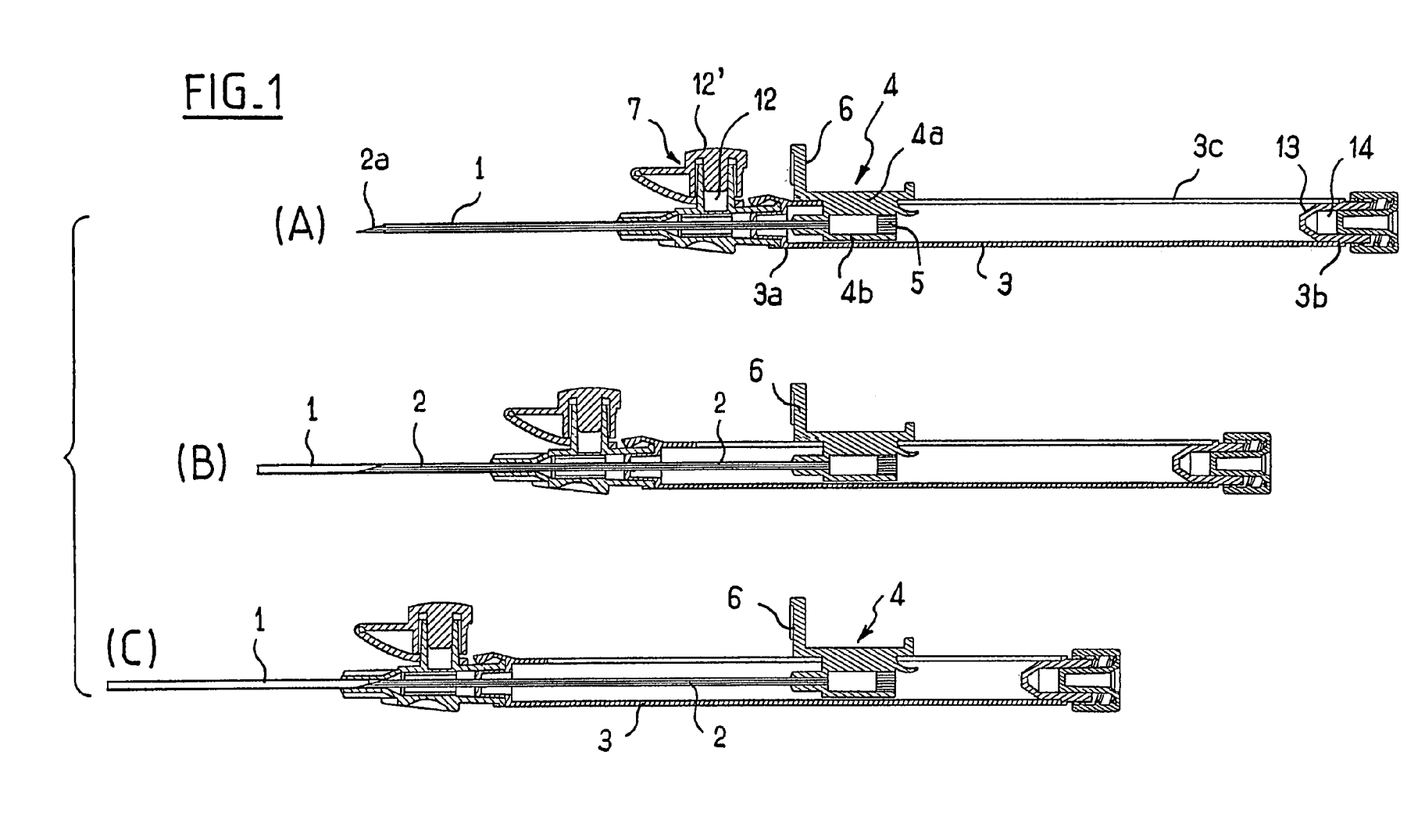
FIG. 1 is a diagram showing the various states of a first embodiment during successive stages A to F of withdrawing the needle into the tubular sheath.
Figure 2:
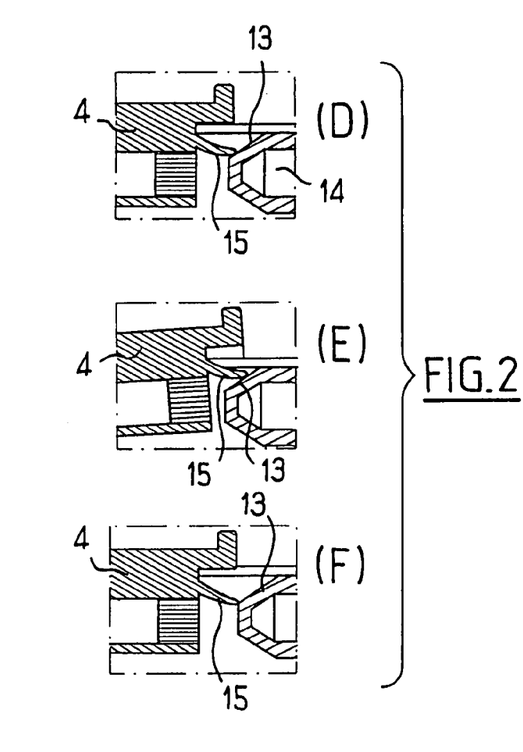
FIG. 2 is a diagram on a larger scale of the proximal end of the tubular sheath during stages D, E, and F in FIG. 1.

In the embodiment of FIGS. 1 and 2, these deflectors are constituted by a ramp (13) formed on a piece (14) engaged in the proximal end (3b) of the sheath and prevented from moving by a stopper (14'). This piece is frustoconical in shape, for example, with its conical wall constituting the ramp. The slider is provided in its internal portion with a resilient tongue (15) directed rearwards and which causes the slider to be deflected on making contact with the ramp, thereby moving the needle off axis (FIGS. 1D, 1E) as the slider engages the ramp.

Figures 10, 11, 12, 13:
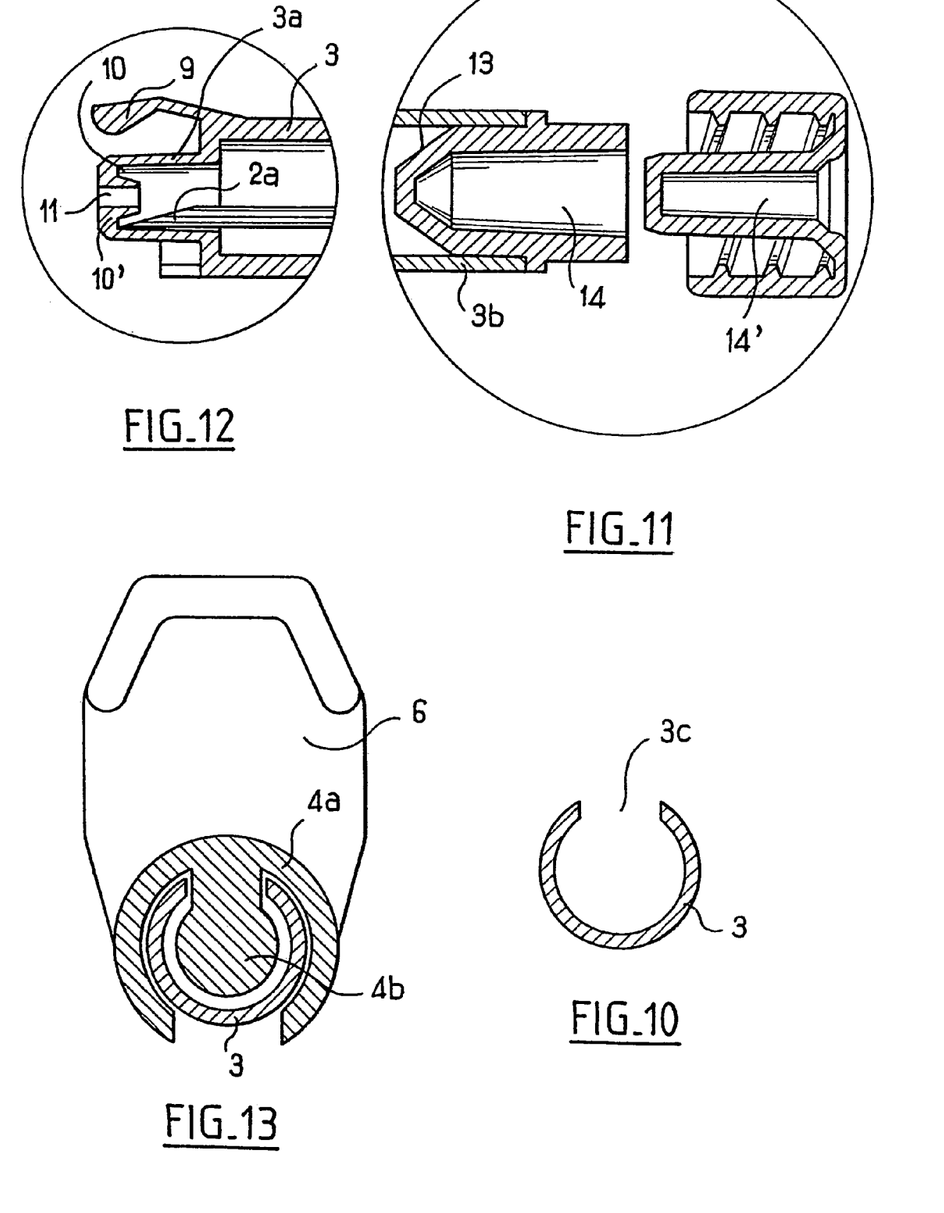
FIG. 10 is a right section through the main part of the sheath on a plane X-X.
FIG. 11 is an axial section on a larger scale of the proximal end of the sheath of FIG. 1 with its stopper which is shown separated in the figure for reasons of clarity.
FIG. 12 is an axial section on a larger scale of the distal end of the sheath in an embodiment in accordance with FIG. 1F, 3F, or 5F.
FIG. 13 is a right section through a slider and a sheath of the invention.

At the end of the stroke, the slider is pushed back in the opposite direction by the tongue so that the chamfered tip of the inclined needle (2a) is received in a cylindrical groove (10) formed inside the distal end (3a) of the sheath around the outlet (11) until it becomes set against the wall (10') at the front of the sheath, thereby preventing the needle from moving (FIG. 1F and FIG. 12).

Figure 3:
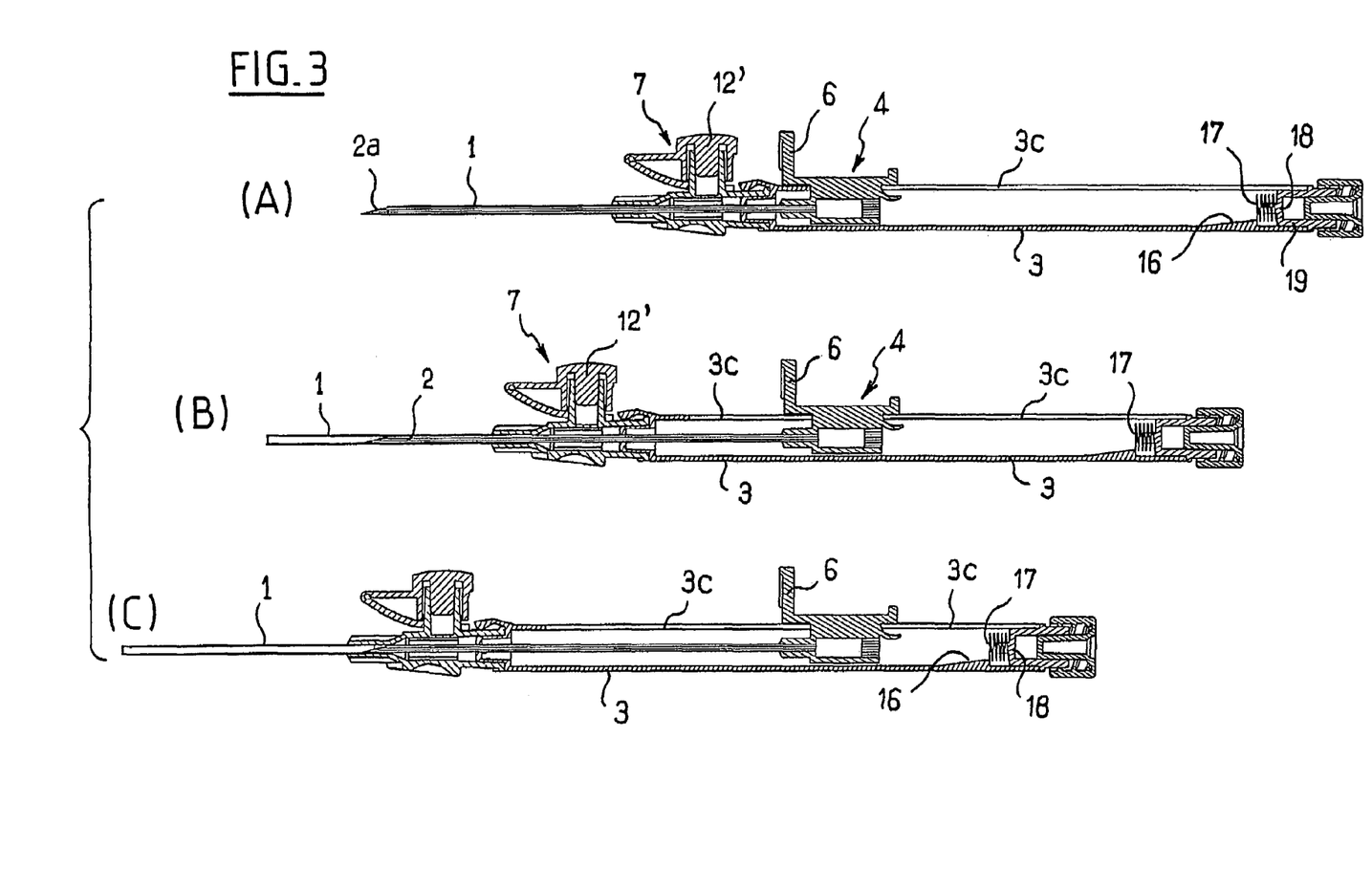
FIG. 3 is a diagram showing the various states of a second embodiment during successive stages A to F of withdrawing the needle into the tubular sheath.
Figure 4:
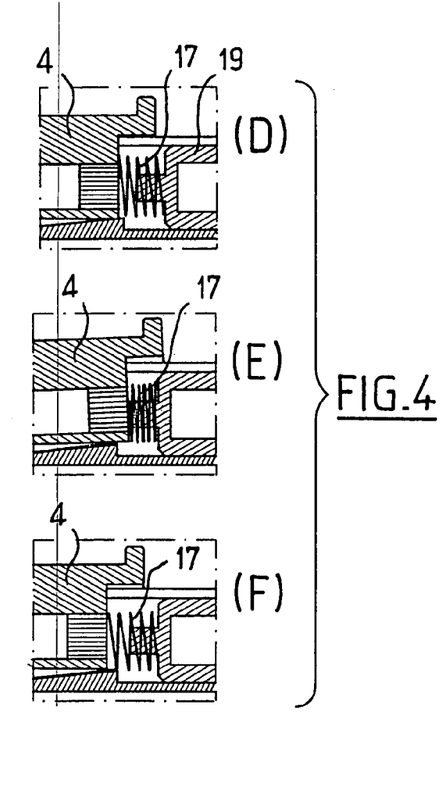
FIG. 4 is a diagram on a larger scale of the proximal end of the tubular sheath during stages D, E, and F of FIG. 3.
Figure 5:
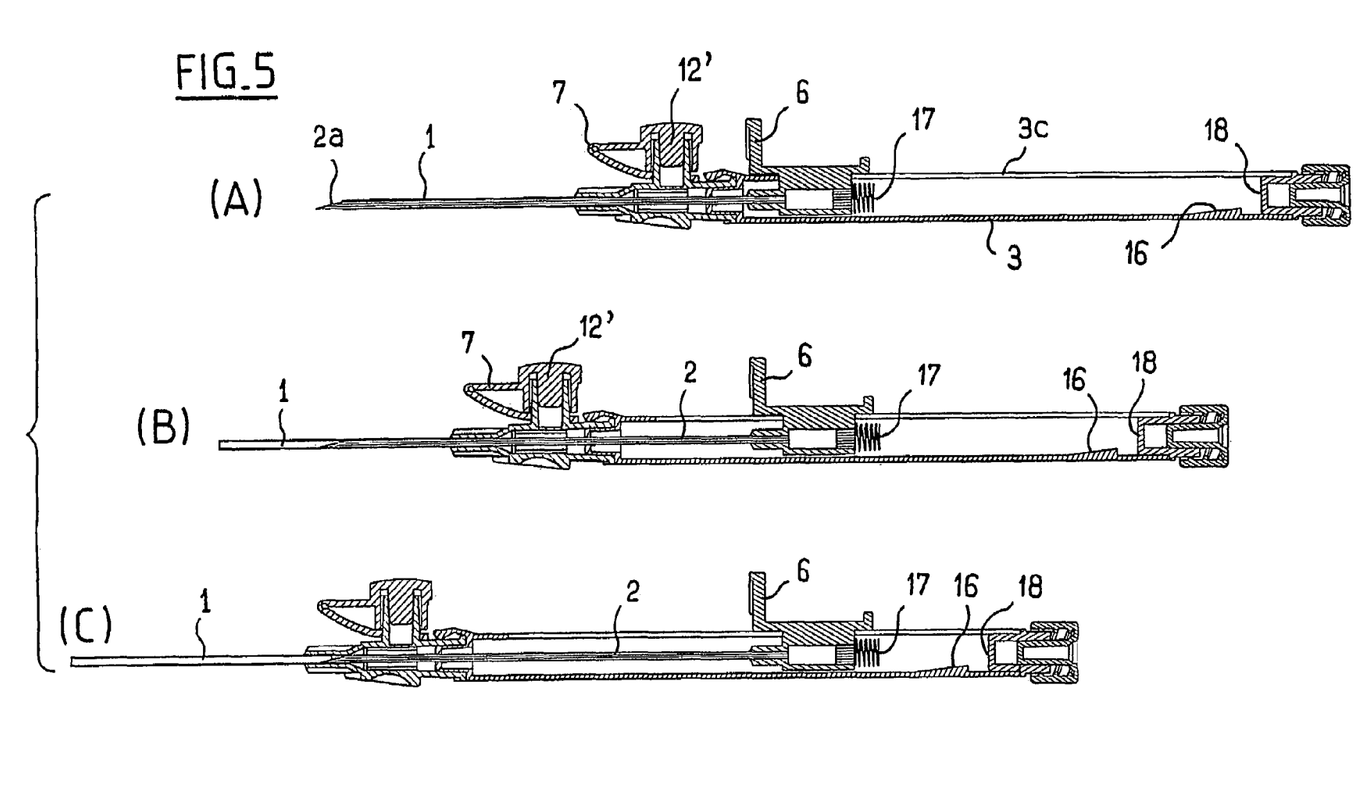
FIG. 5 is a diagram of the various states of a third embodiment during successive stages A to F while withdrawing the needle into the tubular sheath.
Figure 6:
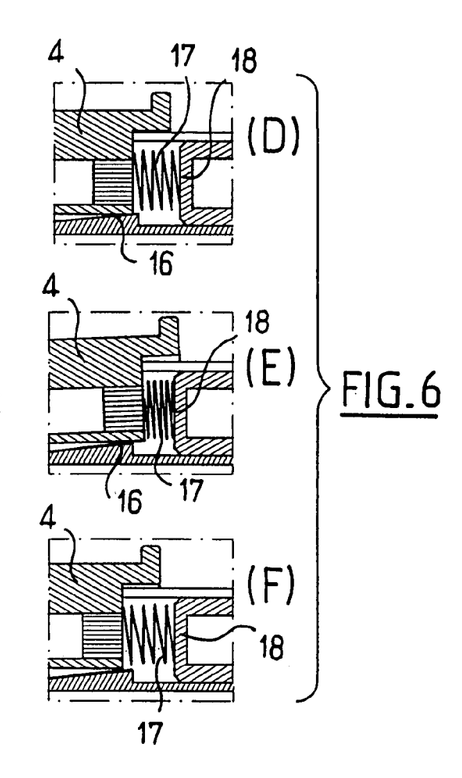
FIG. 6 is a diagram on a larger scale of the proximal end of the tubular sheath during stages D, E, and F of FIG. 5.

In the embodiment of FIGS. 3 and 5, a ramp (16) is formed by an internal projection on the side wall of the sheath close to the proximal end (3b) of the sheath and located on the path followed by the internal portion (4b) of the slider so that the projection causes the slider to be inclined as it passes over the projection (FIGS. 3D, 3E, 5D, 5E). A helical spring (17) placed between the internal portion of the slider and an abutment (18) situated in the proximal end (3b) of the sheath then pushes the slider back sufficiently for the chamfered tip of the needle to become fixed in the wall (10') situated at the front of the sheath (FIGS. 3F, 5F, and 12).

The spring (17) is fixed to the abutment (18) as shown in the embodiment of FIG. 3, or else it is fixed to the internal portion of the slider, as in the embodiment of FIG. 5.

The abutment (18) is constituted by the front face of a piece (18') inserted as a stopper into the proximal end of the sheath.

FIGS. 7 to 9 show successive stages (P1 to P5) in a process of putting a catheter into place, during which the operator uses one hand or both hands to act on the lug (6) of the slider, the cap (12') of the coupling, or the stopper (14'), in order to puncture the skin (P1, P2), progressively withdraw the needle (P3, P4), and separate the sheath containing the needle (P5) from the catheter coupling.

Figure 14:
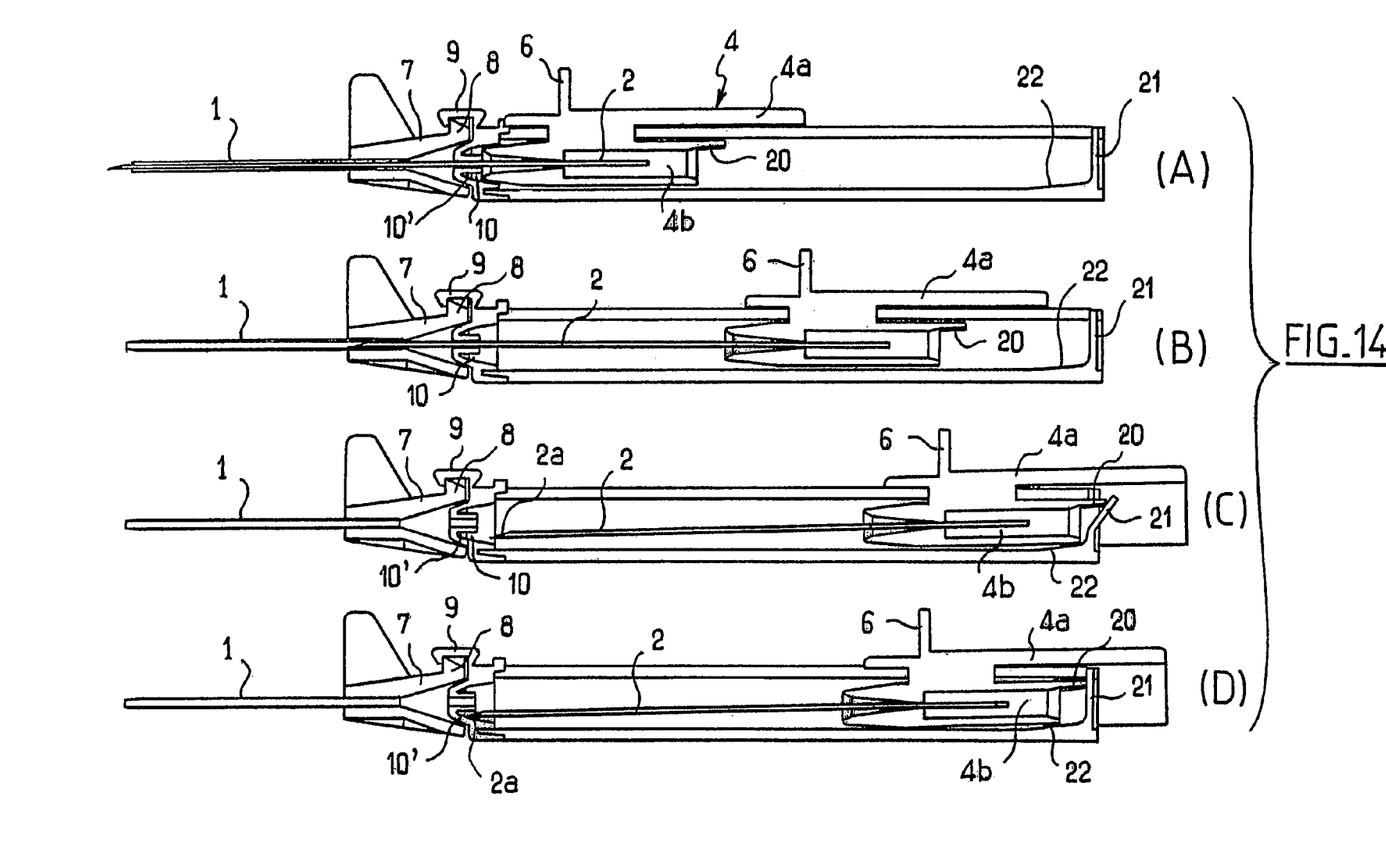
FIG. 14 is a diagram of the various states of a fourth embodiment during successive stages A to D while withdrawing the needle into the tubular sheath.

In the embodiment in FIG. 14, the return means for returning the inclined needle towards the distal end of the sheath comprises a rigid lug (20) projecting towards the proximal end of the sheath over the inner portion (4b) of the slider (4) which constitutes the base of the needle, and a resilient blade (21) disposed in the cross-piece of the proximal end (3b) of the sheath (3) so that said blade, pushed by the lug, after deflection of the needle (FIG. 14C) and after the user has relaxed traction on the slider, pushes the slider back in the opposite direction over a distance that is sufficient for the point of the needle to be received in a wall of the distal end of the sheath or of the coupling (19) present at said end (FIG. 14D). For example, it is blocked in the end wall of a cylindrical groove (10) formed in the coupling mounted at the distal end of the sheath in order to connect the catheter.

Preferably, as in the example shown, the resilient blade is constituted by a wall that is molded integrally with the wall of the sheath, but which is secured to the side wall of the sheath over only a portion of its circumference.

In the embodiment in FIG. 14, the deflector means are constituted by a ramp (22) that is injection molded integrally with the longitudinal wall of the sheath (like the ramp 16 of the embodiment in FIGS. 3 and 5) and with the resilient blade (21) which is secured to the end of said ramp and is not connected anywhere else with the tube.

It should be noted that this embodiment is particularly simple.

The invention is not limited to the embodiments described above.

The invention claimed is:

1. A medical assembly comprising a short catheter, a puncturing needle engaged in the catheter to enable the catheter to be inserted into a body, and a tubular sheath detachably coupled to the catheter to receive the entire needle after the needle has been used for puncturing and once it has been withdrawn from the catheter, the sheath presenting a longitudinal slot between a distal outlet end for coupling to the catheter and an opposite proximal end, and carrying a slider mounted to slide along the slot to control said withdrawal of the needle, the slider presenting an internal portion situated inside the sheath and constituting a base for the needle, and an external portion situated on the sheath and enabling the slider to be pushed manually to cause to it to slide towards said proximal end to a proximal position in which the needle is fully withdrawn into the tube, the sheath comprising a stationary deflector disposed inside the sheath on the path of the slider close to the end of the stroke of the slider towards said proximal end of the sheath, so that contact between the slider and the deflector causes the slider to be inclined and consequently causes the needle to be inclined inside the sheath, and resilient return means provided so as to push the inclined slider back in the opposite direction by a resilient effect until the tip of the inclined needle becomes set in a wall at the distal end of the sheath.

2. An assembly according to claim 1, in which the deflector is a ramp constituted by an internal projection from the side wall of the sheath.

3. An assembly according to claim 2, and including a helical spring disposed between the internal portion of the slider and an abutment disposed in the proximal end of the sheath, said helical spring pushing the inclined slider back at the end of its stroke.

4. An assembly according to claim 3, in which said spring is fixed to the internal portion of the slider.

5. An assembly according to claim 3, in which said spring is fixed to said abutment.

6. An assembly according to claim 2, in which the abutment is the front face of a stopper inserted in the proximal end of the sheath.

7. An assembly according to claim 1, in which said return means are constituted by a rigid lug projecting towards the proximal end of the sheath over the inner portion of the slider, and by a resilient blade disposed at the proximal end of the sheath so that said blade, pushed by the lug, after inclination of the needle, pushes the slider and the needle back in the opposite direction over a distance that is sufficient for the point of the inclined needle to be blocked in the distal end of the sheath.

8. An assembly according to claim 7, in which said distal end of the sheath is provided with a coupling for mounting the catheter, and in which said coupling presents, around the needle outlet of the sheath, a groove for receiving the point of the inclined and pushed-back needle.

9. An assembly according to claim 7, in which said resilient blade is formed by a wall situated in the cross-piece of the proximal end of the sheath, but which is secured to the sheath only over a portion of its circumference.

10. An assembly according to claim 7, in which the sheath comprises deflector means constituted by a ramp constituted by an inside bulge of the side wall of the sheath, and in which said wall which constitutes the resilient blade is injection molded integrally with the end of said ramp.

11. An assembly according to claim 1, in which the distal end of the sheath presents a groove made around a needle outlet of the sheath to receive the tip of the inclined needle.

12. An assembly according to claim 11, having a groove that is formed in a coupling disposed in said distal end for connecting the catheter.

13. An assembly according to claim 1, in which said deflector is constituted by a piece engaged and held in the proximal end of the sheath and presents a ramp on which an internal portion of the slider becomes engaged.

14. An assembly according to claim 13, in which the internal portion of the slider presents a resilient tongue which rubs against said ramp and which acts at the end of the slider stroke to push back the inclined slider.

15. An assembly according to claim 1, in which the short catheter is provided with an inlet coupling which serves as a thrust bearing point for the user and in which the distal end of the coupling of the sheath to the catheter is shaped in order to penetrate into said coupling and to secure said end to the coupling.

16. An assembly according to claim 15, in which the distal end of the sheath is provided with a coupling for connecting it to the catheter, which coupling penetrates into the catheter coupling.

17. An assembly according to claim 1, in which the deflector is constituted by a piece disposed in the proximal end of the sheath.

* * * * *